(12) United States Patent
Kim et al.

(10) Patent No.: US 10,981,937 B2
(45) Date of Patent: Apr. 20, 2021

(54) METHIONINE-METAL CHELATE AND MANUFACTURING METHOD THEREOF

(71) Applicant: CJ CHEILJEDANG CORPORATION, Seoul (KR)

(72) Inventors: Jun-Woo Kim, Seoul (KR); Min Kyu Kang, Seoul (KR); Gyeonghwan Kim, Seoul (KR); Il Chul Kim, Seoul (KR); Juun Park, Seoul (KR); Yong Bum Seo, Seoul (KR); In Sung Lee, Seoul (KR); Jun Young Jung, Seoul (KR); Je-won Hong, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/630,909

(22) PCT Filed: Jul. 6, 2018

(86) PCT No.: PCT/KR2018/007690
§ 371 (c)(1),
(2) Date: Jan. 14, 2020

(87) PCT Pub. No.: WO2019/013497
PCT Pub. Date: Jan. 17, 2019

(65) Prior Publication Data
US 2020/0270276 A1 Aug. 27, 2020

(30) Foreign Application Priority Data
Jul. 14, 2017 (KR) .................. 10-2017-0089640

(51) Int. Cl.
*A23K 20/142* (2016.01)
*C07F 3/00* (2006.01)
*C01F 11/36* (2006.01)
*C05C 5/04* (2006.01)
*C07F 1/00* (2006.01)
*C07F 13/00* (2006.01)

(52) U.S. Cl.
CPC ............ *C07F 3/003* (2013.01); *A23K 20/142* (2016.05); *C01F 11/36* (2013.01); *C05C 5/04* (2013.01); *C07F 1/005* (2013.01); *C07F 13/005* (2013.01)

(58) Field of Classification Search
CPC ........ C07F 3/003; C07F 1/005; C07F 13/005; A23K 20/142; C01F 11/36; C05C 5/04
See application file for complete search history.

(56) References Cited

U.S. PATENT DOCUMENTS

| 2,960,406 A * | 11/1960 | Cardon | A23K 20/30 426/2 |
| 2,973,265 A * | 2/1961 | Gillis | A23K 20/30 426/648 |
| 3,396,104 A * | 8/1968 | Miller | C02F 1/5263 210/725 |
| 4,020,158 A * | 4/1977 | Ashmead | A61K 31/295 514/5.5 |
| 4,073,945 A * | 2/1978 | Bertram | C07F 3/003 426/2 |
| 4,830,716 A * | 5/1989 | Ashmead | C07C 51/41 205/457 |
| 5,182,126 A * | 1/1993 | Vinci | A23K 20/105 426/601 |
| 5,516,925 A * | 5/1996 | Pedersen | A61P 3/00 556/50 |
| 5,795,615 A * | 8/1998 | Nelson | C07C 51/412 426/648 |
| 5,885,610 A * | 3/1999 | Anderson | A23K 40/35 424/438 |
| 6,407,138 B1 * | 6/2002 | Ashmead | C07C 227/16 514/492 |
| 6,426,424 B1 * | 7/2002 | Ashmead | C07C 227/16 556/1 |
| 6,461,651 B1 * | 10/2002 | Leusner | A23L 7/101 426/601 |
| 6,670,494 B1 * | 12/2003 | Trusovs | C07C 51/412 426/74 |
| 6,710,079 B1 | 3/2004 | Ashmead et al. | |
| 7,087,775 B2 * | 8/2006 | Lee | C07C 319/20 556/116 |
| 2002/0136781 A1 * | 9/2002 | Huato | C01G 3/10 424/630 |
| 2004/0137108 A1 * | 7/2004 | Abdel-Monem | A23K 50/10 426/2 |
| 2009/0182044 A1 * | 7/2009 | Ashmed | A61K 31/295 514/494 |
| 2019/0328004 A1 * | 10/2019 | Johnson | A23K 20/142 |
| 2020/0157121 A1 * | 5/2020 | Kim | A23K 20/142 |

FOREIGN PATENT DOCUMENTS

| CN | 102491927 A | 6/2012 | |
| IN | 197924 B * | 1/2006 | |
| IN | 197924 | 2/2007 | |
| JP | 2002-069051 A | 3/2002 | |
| JP | 2010-090064 A | 4/2010 | |
| JP | 2010-90064 A | 4/2010 | |
| KR | 20050076209 A * | 7/2005 | |
| KR | 10-0509141 | 8/2005 | |
| KR | 100509141 B1 * | 8/2005 | ............ B60N 2/667 |
| KR | 10-0583274 | 5/2006 | |
| KR | 10-0860778 | 9/2008 | |
| RU | 2563240 C2 | 9/2015 | |
| WO | 95/13700 A2 | 5/1995 | |

(Continued)

OTHER PUBLICATIONS

CAS Abstract of M. Abdel-Monera et al., US 2004/0137108 (2004) (Year: 2004).*

(Continued)

*Primary Examiner* — Alexander R Pagano
(74) *Attorney, Agent, or Firm* — MH2 Technology Law Group, LLP

(57) ABSTRACT

The present disclosure relates to a preparation method of a methionine-metal chelate, and the methionine-metal chelate, which is prepared by first reacting Ca(OH)$_2$ and methionine and adding metal nitrate, can be widely used as feeds and feed additives.

11 Claims, 2 Drawing Sheets

(56) References Cited

FOREIGN PATENT DOCUMENTS

| WO | 95/137000 A2 | 5/1995 | |
| --- | --- | --- | --- |
| WO | WO-9513700 A2 * | 5/1995 | ........... C07C 319/20 |
| WO | 95/13700 A2 | 5/1999 | |
| WO | 02/30948 A2 | 4/2002 | |
| WO | 2013/136030 A2 | 9/2013 | |

OTHER PUBLICATIONS

Faliah Hassan Ali Al-Jeboori, 5 Journal of Chemical and Pharmaceutical Research, 172-176 (2013) (Year: 2013).*
I. Sakiyan et al., 33 Synthesis and Reactivity in Inorganic and Metal-Organic Chemistry, 971-983 (2003) (Year: 2003).*
K. Vassilev et al., 4 Journal of Biomaterials and Nanobiotechnology, 28-36 (2014) (Year: 2014).*
D. Rusu et al., 60 Rev. Chim., 939-943 (2009) (Year: 2009).*
T. Luo et al., 46 Inorganic Chemistry, 1532-1534 (2007) (Year: 2007).*
S. Fox et al., 46 Inorganic Chemistry, 818-824 (2007) (Year: 2007).*
English-Language Machine Translation KR-100509141-B1 (2005) (Year: 2005).*
English-Language Machine Translation KR-20050076209-A (2005) (Year: 2005).*
International Search Report dated Nov. 7, 2018 from International Application No. PCT/KR2018/007690, 5 pages with English translation.
International Search Report dated Nov. 7, 2018 from International Application No. PCT/KR2018/007690, 5 pages with English translation.
Author unknown, "Separation and Purification", Chemical Society of Japan, Chemical Handbook Application Edition, Jan. 30, 2003, edition 6, p. 176-181, with English Translation.
Eishin Kuno, "Calcium Nitrate CA(NO3)2", Chemical Society of Japan, Synthesis II of Inorganic Compounds, Class 8, May 20, 1984, third edition, pp. 595-596 and 601-604, with English Translation.
Devereux et al., "Preparation and catalase-type activity of manganese (II) amino acid complexes", Polyhedron, 1998, vol. 17, No. 1, pp. 1153-158.
Stanila et al., "Spectroscopic studies of some copper(II) complexes with amino acids", Journal of Molecular Structure, 2007, vol. 834-836, pp. 364-368.

* cited by examiner

[FIG. 1]
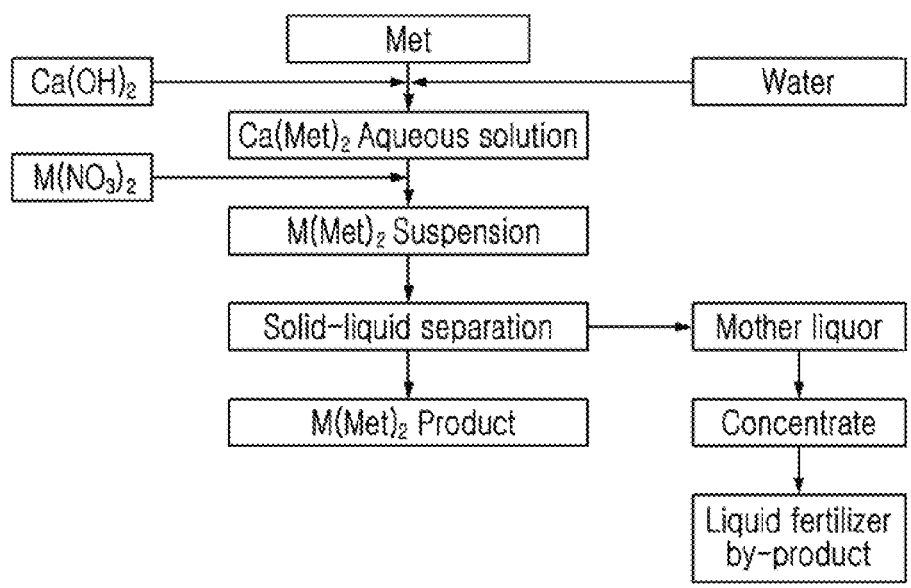

[FIG. 2]
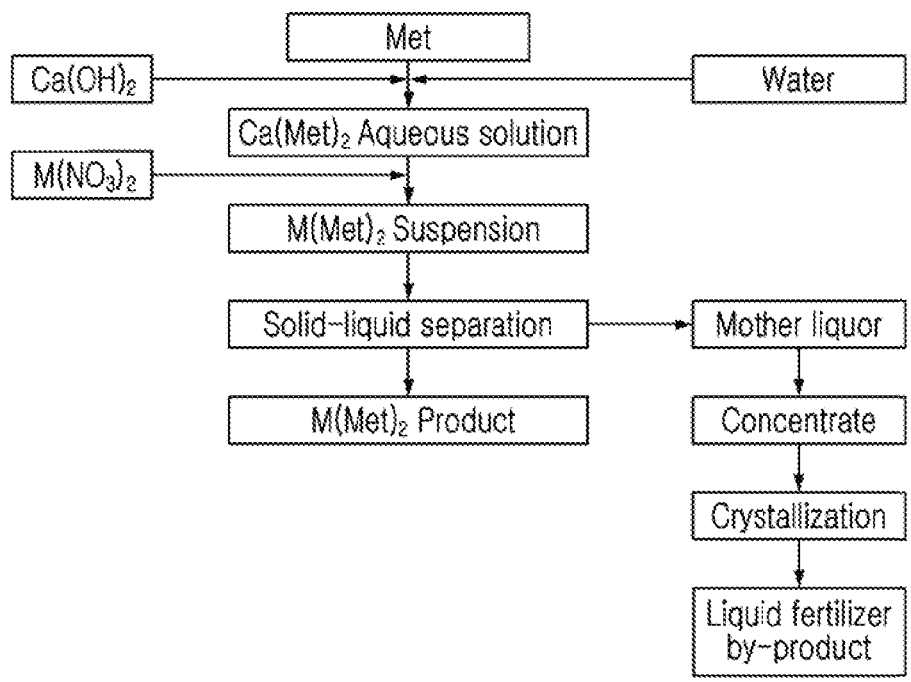

METHIONINE-METAL CHELATE AND MANUFACTURING METHOD THEREOF

CROSS-REFERENCE TO RELATED APPLICATIONS

This application is a U.S. National Stage application of PCT/KR2018/007690 filed 6 Jul. 2018, which claims priority to Korean Patent Application No. 10-2017-0089640 filed 14 Jul. 2017, the entire disclosures of which are herein incorporated by reference.

TECHNICAL FIELD

The present disclosure relates to a methionine-metal chelate and a preparation method thereof.

BACKGROUND ART

Although making up a very small proportion in animal tissues, mineral components such as zinc (Zn), manganese (Mn), copper (Cu), iron (Fe), etc., perform various physiological functions such as forming a skeleton, regulating osmotic pressure in the body, maintaining acid-base equilibrium of body fluids, being involved in the activity as an active agent of the enzymatic system or as a component of enzymes themselves, etc. For example, zinc is an essential material for the growth of livestock and contributes to boosting immunity.

Since such mineral components including zinc cannot be synthesized in the body, proper supply from the outside is necessary, and in the case of livestock, they are provided by combining these ingredients in feeds. However, when minerals are ingested in the inorganic form, such as metal oxides or metal salts, dissociated metal elements can form complexes with other elements competitively, and thus, there is a disadvantage that absorption is inhibited. Therefore, inorganic trace minerals are being supplied in excess of actual livestock demands, and excess minerals that are not absorbed by living organisms are excreted in powder and are reduced to soil, causing deep soil contamination. Therefore, in recent years, the supply of inorganic trace minerals has been limited, such as establishing a legal limit of mineral contents in feed to prevent heavy metal pollution in the environment.

As such, the use of organic trace minerals has been suggested as an alternative, because the absorption rate is high even with using a low amount, which can satisfy the metabolic capacity and reduce the excretion amount. Representative product groups of such organic trace minerals are amino acid-metal complexes and amino acid-metal chelates. Studies are in progress on amino acid-metal chelates, which have relatively high absorption rates in the body.

For example, there are a preparation method of methionine-zinc chelate by mixing methionine with zinc chloride and then adding NaOH (U.S. Pat. No. 7,087,775), a preparation method of methionine-zinc chelate by simultaneously reacting methionine with calcium hydroxide and sulfur zinc sulfate (U.S. Pat. No. 6,710,079), a preparation method of methionine-mineral chelate by mixing a methionine solution and a mineral solution to which a basic substance is added (Korean Patent No. 10-0583274), a preparation method of yeast-mineral chelate by using a yeast liquid and mineral sulfate (Korean Patent No. 10-0860778), a preparation method of methionine-iron chelate by reacting an inorganic iron solution and a methionine solution at a predetermined temperature and pH (Korean Patent No. 10-0509141), etc.

However, ions present in the metal salts used in these methods, such as sulfate ions, etc., have a disadvantage of forming a by-product such as insoluble salts or lowering the yield by interfering with the chelate bond between methionine and the metal.

DISCLOSURE

Technical Problem

As a result of making intensive efforts to find ways to produce methionine-metal chelates with high efficiency, the present applicant confirmed that the preparation method of the present disclosure does not generate insoluble salts and has an effect of greatly improving the recovery rate of the desired methionine-metal chelate, and that $Ca(NO_3)_2$ which is generated as a by-product can be used as a liquid fertilizer or as a solid fertilizer after granulation, thereby completing the present disclosure.

Technical Solution

An object of the present disclosure is to provide a method for preparing a methionine-metal chelate, comprising mixing methionine and $Ca(OH)_2$; and adding metal nitrate to the mixture to produce a methionine-metal chelate.

Another object of the present disclosure is to provide a methionine-metal chelate prepared by the preparation method above.

Still another object of the present disclosure is to provide a feed or a feed additive comprising the methionine-metal chelate.

Still another object of the present disclosure is to provide a method for preparing calcium nitrate ($Ca(NO_3)_2$), comprising mixing methionine and $Ca(OH)_2$; adding metal nitrate to the mixture to produce a methionine-metal chelate; separating the produced methionine-metal chelate; and concentrating a filtrate from which the methionine-metal chelate is separated.

Advantageous Effect

The preparation method of methionine-metal chelates in the present disclosure can be widely used in the feed or feed additive industry of livestock, because the formation of insoluble salts as by-products is prevented, and the title compound can be obtained with high efficiency without additional processes for removing the insoluble salts above.

BRIEF DESCRIPTION OF DRAWINGS

FIG. 1 is a diagram schematically illustrating a process for preparing a methionine-metal chelate using metal nitrate as a metal raw material and a process for obtaining a liquid fertilizer as a by-product.

FIG. 2 is a diagram schematically illustrating a process for preparing a methionine-metal chelate using metal nitrate as a metal raw material and a process for obtaining a solid fertilizer as a by-product.

BEST MODE

In one aspect of achieving the object above, the present disclosure provides a method for preparing a methionine-metal chelate, comprising mixing methionine and $Ca(OH)_2$; and adding metal nitrate to the mixture to produce a methionine-metal chelate.

The present disclosure rests on discovering that in preparing methionine-metal chelates, the recovery rate of methionine-metal chelates can be significantly improved compared to the existing method of using sodium hydroxide or hydrochloride, when methionine is first reacted with calcium hydroxide or calcium oxide to form a methionine-calcium chelate and then reacted with nitrate of the desired metal to prepare a methionine-metal chelate. Further, as Ca(NO$_3$)$_2$ is formed as a by-product from the preparation method of the present disclosure, it can be used as a liquid or solid fertilizer, etc. by additionally performing a step of concentrating a filtrate from which methionine-metal chelates are separated, and thus an environmentally friendly process can be provided that can minimize the generation of metal waste.

As used herein, the term "methionine-metal chelate" may be a compound having a heterocyclic ring structure in which metal ions and methionine are bonded by coordinate covalent bonds and ionic bonds. For example, when the metal is a divalent metal such as zinc, methionine-zinc chelate may be formed in a structure as shown in Chemical Formula 1 by combining methionine and zinc at a molar ratio of 2:1.

[Chemical Formula 1]

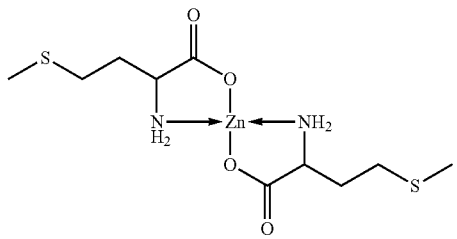

As shown in Chemical Formula 1 above, methionine-metal chelate compounds are not charged, which contributes to increased bioavailability. In addition, even when used less compared to inorganic trace minerals, their in vivo absorption rates are high, and it can help to prevent environmental pollution by satisfying the metabolic capacity and reducing the amount of minerals excreted in livestock excrements.

As used herein, the term "methionine" is one type of essential amino acids in living organisms, and it is an important amino acid involved in the in vivo methyl transfer reaction and serves to provide sulfur to living organisms. The methionine may be L-methionine or DL-methionine, and may be used in an aqueous methionine solution in the preparation method of the present disclosure. For example, the methionine aqueous solution may be a methionine aqueous solution prepared by using water, specifically, distilled water as a solvent. In this case, the concentration of methionine may be, for example, 50 g/L to 300 g/L, specifically, 120 g/L to 240 g/L, but is not limited thereto.

In the preparation method of the present disclosure, the step of mixing methionine and Ca(OH)$_2$ may be performed by heating as needed to completely dissolve methionine. The heating temperature may be 100° C. or less, specifically, 50° C. or less, but is not limited thereto.

As used herein, the term "metal nitrate" is a compound composed of metal ions and nitrate ions represented by the formula M(NO$_3$)$_x$ (x=an integer of 1 to 6), and the number of nitrate ions bound to the metal can be determined by the type of metals and/or oxidation number. For example, the metal in the metal nitrate may be one or more metal selected from the group consisting of copper (Cu), zinc (Zn), manganese (Mn), magnesium (Mg), chromium (Cr), and cobalt (Co). For example, the metal nitrate may be Cu(NO$_3$)$_2$, Zn(NO$_3$)$_2$, Mn(NO$_3$)$_2$, Mg(NO$_3$)$_2$, Cr(NO$_3$)$_2$, or Co(NO$_3$)$_3$, but is not limited thereto. In addition, the metal nitrate may be used in the form of anhydride or hydrate, but is not limited thereto. For example, in the case of zinc nitrate, Zn(NO$_3$)$_2$, which is an anhydride, or Zn(NO$_3$)$_2$.6H$_2$O, which is a hexahydrate, or Zn(NO$_3$)$_2$.7H$_2$O, which is a heptahydrate, can be used without limitation, and it does not affect the yield and/or the quality of the finally prepared methionine-zinc chelates.

For example, the metal nitrate may be added at an equivalence ratio of 0.3 or more relative to methionine. Specifically, it can be added at an equivalence ratio of 0.3 or more and 3.0 or less, more specifically, 0.4 or more and 0.7 or less, but is not limited thereto. For example, when a metal chloride salts containing a divalent metal is used, assuming that all atoms and molecules participate in the reaction, two methionine molecules may bind to one metal atom as shown in Chemical Formula 1. Therefore, when metal nitrate is added at an equivalence ratio of 0.5 relative to methionine, both methionine and the metal may appear to participate in the chelate formation. However, the equivalence ratio of metal nitrate relative to methionine, which can exhibit an optimal yield depending on variables such as other ions substantially existing in the reaction solution, pH of the solution, temperature, etc. may be in the range above considering some errors based on the theoretical value of 0.5.

In addition, the preparation method of the present disclosure may further include purifying the generated methionine-metal chelate after producing a methionine-metal chelate. The purifying step may be carried out by a person skilled in the art to choose from known methods, for example, filtration, centrifugation, anion exchange chromatography, crystallization. HPLC, etc. may be used. For example, since calcium nitrate, which is a by-product of the preparation method in the present disclosure, has high solubility in water, methionine-metal chelates whose solubility is relatively low may be separated using a solid-liquid separator, for example, a filtration, centrifugal, etc. solid-liquid separator, but is not limited thereto.

Furthermore, the preparation method of the present disclosure may further include drying a methionine-metal chelate. The drying step may be carried out using any method known in the art without limitation. For example, methods such as natural drying, heat drying, air drying, hot air drying, spray drying, drum drying, or rotary vacuum drying, etc. may be used, but are not limited thereto.

Specifically, upon spray drying, white powder can be obtained by drying under the conditions of inlet temperature of 180° C., outlet temperature of 90° C., and upon drying using a drum drier, white powder can be obtained by drying under the conditions of an internal temperature of 150° C. and a pressure of about 3 kgf/cm$^2$, and upon drying in a rotary vacuum drier, white powder can be obtained by vacuum drying under the conditions of an internal temperature of 55° C. to 70° C. and a vacuum of 650 mm/Hg.

In another aspect, the present disclosure provides a methionine-metal chelate prepared by the preparation method above.

In another aspect, the present disclosure provides a feed or a feed additive including the methionine-metal chelate.

As used herein, the term "feed" refers to food that is ingested by an animal, and specifically, may refer to a material that supplies organic or inorganic nutrients necessary to maintain the life of the animal or to produce meat, milk, etc. The feed may include feed additives and may be prepared in various forms known in the art.

The type of the feed is not particularly limited, and a feed that is conventionally used in the corresponding technical field may be used. Non-limiting examples of the feed include vegetable feeds such as cereals, root plants, food processing by-products, algae, fibers, oils, starches, gourds, grain by-products, etc.; and animal feeds such as proteins, inorganics, fats and oils, minerals, single-cell proteins, zooplankton, or food, etc. These may be used alone or in combination of two or more thereof.

As used herein, the term "feed additive" refers to a substance added to a feed composition. The feed additive may be to improve productivity or promote health of a target animal, but is not limited thereto. The feed additive may correspond to a supplementary feed under the Control of Livestock and Fish Feed Act.

The feed additive of the present disclosure may be used by further mixing one or more ingredients of organic acids such as citric acid, fumaric acid, adipic acid, lactic acid, etc. and natural antioxidants such as polyphenols, catechins, tocopherols, vitamin C, green tea extract, chitosan, tannic acid, etc., and depending on needs, other conventional additives such as buffers, bacteriostatic agents, etc. may be added. In addition, it may be formulated into a liquid, capsule, granule, or tablet as needed.

The feed or feed additive may further include substances exhibiting various effects such as supplementation of nutrients and prevention of weight loss, enhancement of digestive availability of fibers in the feed, improvement of oil quality, prevention of reproductive disorders and improvement in conception rates, prevention of high-temperature stress in summer, etc. For example, it may be used with nutritional supplements, growth promoters, digestive absorption accelerators, and disease prevention agents, in addition to the main components such as various supplements such as amino acids, inorganic salts, vitamins, antioxidants, antifungal, microbial preparations, etc., vegetable protein feeds such as milled or crushed wheat, barley, corn, etc., animal protein feeds such as powdered blood, powdered meat, powdered fish, etc., animal fats and vegetable fats.

The feed and feed additive of the present disclosure may be fed to a number of animals, including mammals and poultry. These can be used in commercially important mammals such as pigs, cattle, goats, etc., and livestock such as dogs, cats, etc., but are not limited thereto.

In another aspect, the present disclosure provides a method for preparing calcium nitrate ($Ca(NO_3)_2$), comprising mixing methionine and $Ca(OH)_2$; adding metal nitrate to the mixture to produce a methionine-metal chelate; separating the produced methionine-metal chelate; and concentrating a filtrate from which the methionine-metal chelate is separated.

The preparation method of calcium nitrate in the present disclosure may further include a step of drying, granulating, or crystallizing after the concentrating step, but is not limited thereto. The drying, granulating, or crystallizing step may be carried out using any method known in the art without limitation.

For example, the liquid itself containing a high concentration of calcium nitrate obtained through the concentrating step may be used as a liquid fertilizer, and by additionally performing a step of drying, granulating, or crystallizing, solid calcium nitrate may be obtained and used as a solid fertilizer.

As previously described, in the step of mixing methionine and CaO or $Ca(OH)_2$ and the step of producing a methionine-metal chelate by adding metal nitrate to the mixture, a methionine-metal chelate which is the title compound and $Ca(NO_3)_2$ which is a by-product are produced. Since the $Ca(NO_3)_2$ is a water-soluble substance and has a significantly higher solubility than methionine-metal chelates, methionine-metal chelates may be selectively crystallized by adjusting the temperature of the solution, etc. As a filtrate from which methionine-metal chelates are separated has a large amount of $Ca(NO_3)_2$, which is a by-product, dissolved therein, $Ca(NO_3)_2$ can be obtained from a mother liquor through an additional process of concentrating and/or selectively granulating. In addition to helping to reduce process waste, $Ca(NO_3)_2$ prepared as above can be used not only as a fertilizer capable of supplying calcium and nitrogen at the same time, but also as a latex coagulant, renewable refrigeration packs, etc., in wastewater pretreatment to prevent odor generation or in acceleration of concrete mixing, thereby creating additional economic values.

DETAILED DESCRIPTION

Hereinafter, the present disclosure will be described in more detail in the following examples. However, these examples are only to help the understanding of the present disclosure, and the present disclosure is not limited thereto.

In the examples of the present disclosure, the purity represents a percentage of the sum of the masses of the target metal and methionine included in the final dried solid relative to the mass of the final dried solid, and the recovery rate represents a percentage of the sum of the masses of the target metal and methionine included in the final dried solid relative to the sum of the entire masses of the target metal and methionine that were introduced in the reaction.

Comparative Example 1: Preparation of Methionine-Zinc Chelate According to Method of Adding NaOH after Dissolving Metal Salt and Methionine A methionine-zinc chelate was prepared using the method described in U.S. Pat. No. 7,087,775. Specifically, 2 L of $ZnCl_2$ aqueous solution was prepared, and L-methionine was dissolved in $ZnCl_2$:L-methionine=1:2 molar ratio so that the concentration of L-methionine was 120 g/L. NaOH was added to the corresponding aqueous solution in the same equivalence ratio as L-methionine to prepare a suspension containing L-methionine-zinc chelate particles. The corresponding suspension was separated by vacuum filter to obtain L-methionine-zinc chelate. After drying, the content was 79.1% methionine and 17.8% zinc, and in this case, the purity was 96.9% and the recovery rate was 78.3%.

Comparative Example 2: Preparation of Methionine-Zinc Chelate According to Method of Synthesis by Simultaneously Mixing $Ca(OH)_2$/Metal Sulfate/Methionine A methionine-zinc chelate was prepared by using the method described in U.S. Pat. No. 6,710,079. Specifically, 120 g of L-methionine was mixed with $Ca(OH)_2$ and $ZnSO_4$ heptahydrate at an equivalence ratio of 0.5 relative to L-methionine to prepare a powder mixture. The corresponding mixture was placed in a closed container and reacted at 80° C. for 12 hours. After cooling to room temperature, a mixture of L-methionine chelate and $CaSO_4$ was obtained.

After drying, the content was 59.2% methionine, 13.0% zinc, 7.8% calcium, and 18.0% $SO_4$, and in this case, methionine-zinc chelate was precipitated with an insoluble salt ($CaSO_4$), and the purity calculated by adding the contents of methionine and zinc was 73.7%, and in order to achieve a purity of 95% or more, an additional purification process was required. The final recovery rate was 97.2%.

Comparative Example 3: Preparation of Methionine-Manganese Chelate According to Method of Adding NaOH after Dissolving Metal Salt and Methionine A methionine-manganese chelate was prepared using the method described in U.S. Pat. No. 7,087,775. Specifically, 2 L of $MnCl_2$ aqueous solution was prepared, and L-methionine was dissolved in $MnCl_2$:L-methionine=1:2 molar ratio so that the concentration of L-methionine was 120 g/L. NaOH was added to the corresponding aqueous solution in the same equivalence ratio as L-methionine to prepare a suspension containing L-methionine-manganese chelate particles. The corresponding suspension was separated by vacuum filter to obtain L-methionine-manganese chelate. After drying, the content was 67.2% methionine and 8.8% manganese, and in this case, the purity was 76.0% and the recovery rate was 7.1%.

Comparative Example 4: Preparation of Methionine-Copper Chelate According to Method of Adding NaOH after Dissolving Metal Salt and Methionine A methionine-copper chelate was prepared using the method described in U.S. Pat. No. 7,087,775. Specifically, 2 L of $CuCl_2$ aqueous solution was prepared, and L-methionine was dissolved in $CuCl_2$:L-methionine=1:2 molar ratio so that the concentration of L-methionine was 120 g/L. NaOH was added to the corresponding aqueous solution in the same equivalence ratio as L-methionine to prepare a suspension including L-methionine-copper chelate particles. The corresponding suspension was separated by vacuum filter to obtain L-methionine-copper chelate. After drying, the content was 82.4% methionine and 16.8% copper, and in this case, the purity was 99.2% and the recovery rate was 28.9%.

Example 1: Preparation of Methionine-Zinc Chelate According to Method of Adding Metal Nitrate after First Dissolving Ca(OH) and Methionine (Met:Zn=1:0.4)

An L-methionine-calcium chelate aqueous solution was prepared by adding $Ca(OH)_2$ at an equivalence ratio of 0.5 relative to the L-methionine in 2 L of an aqueous suspension of L-methionine concentration 150 g/L. Thereafter, $Zn(NO)_2.6H_2O$, which is a hexahydrate, was added to the corresponding aqueous solution at an equivalence ratio of 0.4 relative to L-methionine, thereby obtaining L-methionine-zinc chelate. After drying, the content was 81.8% methionine and 17.8% zinc, and in this case, the purity was 99.6%, and the recovery rate was 90.2/%.

Example 2: Preparation of Methionine-Zinc Chelate According to Method of Adding Metal Nitrate after First Dissolving Ca(OH) and Methionine (Met:Zn=1:0.5)

An L-methionine-calcium chelate aqueous solution was prepared by adding $Ca(OH)_2$ at an equivalence ratio of 0.5 relative to the L-methionine in 2 L of an aqueous suspension of L-methionine concentration 154 g/L. Thereafter, $Zn(NO_3)_2.6H_2O$ was added to the corresponding aqueous solution at an equivalence ratio of 0.5 relative to L-methionine, thereby obtaining an L-methionine-zinc chelate. After drying, the content was 81.4% methionine and 18.1% zinc, and in this case, the purity was 99.5%, and the recovery rate was 93.6%.

Example 3: Preparation of Methionine-Zinc Chelate According to Method of Adding Metal Nitrate after First Dissolving Ca(OH)₂ and Methionine (Met:Zn=1:0.7)

An L-methionine-calcium chelate aqueous solution was prepared by adding $Ca(OH)_2$ at an equivalence ratio of 0.5 relative to the L-methionine in 2 L of an aqueous suspension of L-methionine concentration 154 g/L. Thereafter, $Zn(NO_3)_2.6H_2O$ was added to the corresponding aqueous solution at an equivalence ratio of 0.7 relative to L-methionine, thereby obtaining an L-methionine-zinc chelate. After drying, the content was 81.4% methionine and 18.2% zinc, and in this case, the purity was 99.6%, and the recovery rate was 94.6%.

Example 4: Preparation of DL-Methionine-Zinc Chelate According to Method of Adding Metal Nitrate after First Dissolving Ca(OH)₂ and DL-Methionine A DL-methionine-calcium chelate aqueous solution was prepared by adding $Ca(OH)_2$ at an equivalence ratio of 0.5 relative to the DL-methionine in 2 L of an aqueous suspension of DL-methionine concentration 154 g/L. Thereafter, $Zn(NO)_2.6H_2O$ was added to the corresponding aqueous solution at an equivalence ratio of 0.5 relative to DL-methionine, thereby obtaining a DL-methionine-zinc chelate. After drying, the content was 81.9% methionine and 17.9% zinc, and in this case, the purity was 99.8%, and the recovery rate was 93.9%.

Example 5: Preparation of Methionine-Zinc Chelate According to Method of Adding Metal Nitrate after First Dissolving Ca(OH)₂ and an Increased Amount of Methionine An L-methionine-calcium chelate aqueous solution was prepared by adding $Ca(OH)_2$ at an equivalence ratio of 0.5 relative to the L-methionine in 2 L of an aqueous suspension of L-methionine concentration 240 g/L. Thereafter, $Zn(NO_3)_2.6H_2O$ was added to the corresponding aqueous solution at an equivalence ratio of 0.5 relative to L-methionine, thereby obtaining an L-methionine-zinc chelate. After drying, the content was 81.6% methionine and 18.0% zinc, and in this case, the purity was 99.6%, and the recovery rate was 94.9%.

Example 6: Preparation of Methionine-Manganese Chelate According to Method of Adding Metal Nitrate after First Dissolving Ca(OH)₂ and Methionine An L-methionine-calcium chelate aqueous solution was prepared by adding $Ca(OH)_2$ at an equivalence ratio of 0.5 relative to the L-methionine in 2 L of an aqueous suspension of L-methionine concentration 120 g/L. Thereafter, $Mn(NO_3)_2$ was added to the corresponding aqueous solution at an equivalence ratio of 0.5 relative to L-methionine, thereby obtaining an L-methionine-manganese chelate. After drying, the content was 59.4% methionine and 9.9% manganese, and in this case, the purity was 69.3%, and the recovery rate was 45.4%.

Example 7: Preparation of Methionine-Copper Chelate According to Method of Adding Metal Nitrate after First Dissolving Ca(OH)$_2$ and Methionine An L-methionine-calcium chelate aqueous solution was prepared by adding Ca(OH) at an equivalence ratio of 0.5 relative to the L-methionine in 2 L of an aqueous suspension of L-methionine concentration 120 g/L. Thereafter, Cu(NO$_3$)$_2$.3H$_2$O was added to the corresponding aqueous solution at an equivalence ratio of 0.5 relative to L-methionine, thereby obtaining an L-methionine-copper chelate. After drying, the content was 82.0% methionine and 17.1% copper, and in this case, the purity was 99.1%, and the recovery rate was 95.7%.

Example 8: Preparation of Liquid Fertilizer Containing Ca(NO$_3$)$_2$ Using Methionine-Metal Chelate Reaction by-Product After preparing an L-methionine-zinc chelate according to Example 2 above, the title compound, L-methionine-zinc chelate, was separated and the remaining mother liquor was further concentrated 8 times to prepare a liquid fertilizer including Ca(NO$_3$, a by-product of the reaction, as a main component. The content of the solids remaining after evaporating all of the liquid fertilizer by-products at 120° C. was 22.2% calcium, 68.6% NO$_3$, 7.6% methionine, and 1.2% zinc.

Example 9: Preparation of Solid Fertilizer Containing Ca(NO$_3$)$_2$ Using Methionine-Metal Chelate Reaction by-Product After preparing an L-methionine-zinc chelate according to Example 2 above, the title compound, L-methionine-zinc chelate, was separated, and a liquid fertilizer in which the remaining mother liquor was concentrated was sprayed in a fluid bed dryer (180° C.) to prepare a solid fertilizer in the form of granular crystals.

From a series of the comparative examples and examples above, compared to the method of adding NaOH in the mixture of metal salts and methionine, which is a conventional preparation method of methionine-metal chelate, or the method of using metal sulfate, it was confirmed that the purity and recovery rate of methionine-metal chelate could be significantly increased by using a preparation method of reacting with metal nitrate after forming the methionine-calcium chelate of the present disclosure. Specifically, in Comparative Example 1 using NaOH, the purity was relatively high at 96.9%, but the recovery rate was only 78.3%. In Comparative Example 2 using sulfate, calcium sulfate, which is an insoluble salt, was precipitated together and the purity was only 73.7%, and an additional purification step was required. However, in Example 2 in which methionine and a zinc compound were reacted at the same molar ratio using the preparation method of the present disclosure, the significantly high purity of 99.5% and the recovery rate of 93.6% were shown without an additional purification step.

Meanwhile, as a result of changing the type of metal to prepare a methionine-metal chelate and confirming the recovery rate thereof, compared to preparing a methionine-metal chelate using the conventional method of using NaOH as in Comparative Examples 3 and 4, a methionine-manganese chelate and a methionine-copper chelate were prepared at increased recovery rates of 38.3% and 66.8%, respectively, when prepared according to Examples 6 and 7 of the present disclosure.

Further, in the preparation process of a methionine-metal chelate according to the present disclosure, a methionine-metal chelate which is the title compound was recovered from the reaction solution, and the remaining mother liquor contained Ca(NO$_3$)$_2$ as a main component, and it was confirmed that as in Example 8, Ca(NO$_3$)$_2$ was obtained in the form of granular particles by concentrating and granulating the mother liquor.

As such, the process of the present disclosure can prepare a methionine-metal chelate at a high yield, which can be used as feed and feed additive, and Ca(NO$_3$)$_2$ which is produced as a by-product of the process can be utilized as feed, etc. by granulation through concentration and an additional granulation process.

From the above description, those skilled in the art will appreciate that the present disclosure can be implemented in other specific forms without changing the technical spirit or essential features. In this regard, the examples described above are illustrative in all respects and should be understood as not limiting. The scope of the present disclosure should be construed as including the meaning and scope of the following claims rather than the detailed description, and all changes or modifications derived from the equivalent concepts.

The invention claimed is:

1. A method for preparing a methionine-metal chelate, comprising:
   mixing methionine and Ca(OH)$_2$; and
   adding metal nitrate to the mixture to produce a methionine-metal chelate.

2. The method of claim 1, wherein the methionine is L-methionine or DL-methionine.

3. The method of claim 1, wherein a metal in the metal nitrate is one or more metal selected from the group consisting of copper (Cu), zinc (Zn), and manganese (Mn).

4. The method of claim 1, wherein the metal nitrate is added at an equivalence ratio of 0.3 or more and 3.0 or less.

5. The method of claim 1, further comprising purifying the produced methionine-metal chelate.

6. The method of claim 1, further comprising drying the methionine-metal chelate.

7. A feed or feed additive comprising the methionine-metal chelate prepared by the method of claim 1.

8. A method for preparing calcium nitrate (Ca(NO$_3$)$_2$), comprising:
   mixing methionine and Ca(OH)2;
   adding metal nitrate to the mixture to produce a methionine-metal chelate;
   separating the produced methionine-metal chelate; and
   concentrating a filtrate from which the methionine-metal chelate is separated.

9. The method of claim 8, wherein a metal in the metal nitrate is one or more metal selected from the group consisting of copper (Cu), zinc (Zn), and manganese (Mn).

10. The method of claim 8, further comprising drying, granulating, or crystallizing after the concentrating.

11. The method of claim 8, wherein the calcium nitrate is a fertilizer additive.

* * * * *